(12) United States Patent
Medvedev

(10) Patent No.: US 11,366,088 B2
(45) Date of Patent: Jun. 21, 2022

(54) SYSTEM AND METHOD FOR OZONE CONCENTRATION MEASUREMENT IN ICE

(71) Applicant: OWS AGRI LIMITED, London (GB)

(72) Inventor: Dmitry Medvedev, Fort Worth, TX (US)

(73) Assignee: OWS AGRI LIMITED, London (GB)

( * ) Notice: Subject to any disclaimer, the term of this patent is extended or adjusted under 35 U.S.C. 154(b) by 214 days.

(21) Appl. No.: 16/767,350

(22) PCT Filed: Jan. 23, 2018

(86) PCT No.: PCT/US2018/014841
§ 371 (c)(1),
(2) Date: May 27, 2020

(87) PCT Pub. No.: WO2019/147220
PCT Pub. Date: Aug. 1, 2019

(65) Prior Publication Data
US 2020/0393433 A1    Dec. 17, 2020

(51) Int. Cl.
*G01N 33/00* (2006.01)
*G01N 21/33* (2006.01)
(Continued)

(52) U.S. Cl.
CPC ......... *G01N 33/0039* (2013.01); *G01N 21/33* (2013.01); *G01N 2021/3155* (2013.01); *G01N 2033/1873* (2013.01)

(58) Field of Classification Search
CPC ............... G01N 33/0039; G01N 21/33; G01N 2021/3155; G01N 2033/1873;
(Continued)

(56) References Cited

U.S. PATENT DOCUMENTS

| 3,700,468 A | 10/1972 | Shore et al. |
| 4,507,253 A | 3/1985 | Wiesmann |

(Continued)

FOREIGN PATENT DOCUMENTS

| DE | 4342624 C1 | 6/1995 |
| KR | 20010055638 A | 7/2001 |

OTHER PUBLICATIONS

International Search Report and Written Opinion for the International Patent Application No. PCT/US18/13797, dated May 10, 2018, 7 pages.

(Continued)

*Primary Examiner* — Jennifer Wecker
*Assistant Examiner* — Oyeleye Alexander Alabi
(74) *Attorney, Agent, or Firm* — KDB Firm PLLC

(57) ABSTRACT

A system for determining ozone concentration in ice includes at least one emitter and first and second detectors. The emitter can be a light source including visible and UV light components, or the emitter can be a first emitter for emitting UV light and a second emitter for emitting visible light. The UV and visible light components can be directed through a sample of ice. The transmitted UV and visible light components can be detected by UV and visible light detectors. The amount of UV and visible light received by the detectors can be compared to levels of UV and visible light emitted by the emitter(s) can be used to determine the concentration of a dissolved gas (e.g., ozone) in the sample of ice.

20 Claims, 4 Drawing Sheets

(51) Int. Cl.
*G01N 21/31* (2006.01)
*G01N 33/18* (2006.01)

(58) Field of Classification Search
CPC .... G01N 21/255; G01N 21/314; G01N 21/94; G01N 33/0004
See application file for complete search history.

(56) References Cited

U.S. PATENT DOCUMENTS

| | | | |
|---|---|---|---|
| 4,549,477 | A | 10/1985 | McCabe |
| 4,732,480 | A | 3/1988 | Fortunato et al. |
| 5,334,355 | A | 8/1994 | Faddis |
| 5,420,432 | A | 5/1995 | Manook et al. |
| 5,632,333 | A | 5/1997 | Imamura et al. |
| 5,868,999 | A | 2/1999 | Karlson |
| 5,972,714 | A | 10/1999 | Roland et al. |
| 6,171,625 | B1 | 1/2001 | Denvir et al. |
| 6,485,769 | B2 | 11/2002 | Audy et al. |
| 6,518,574 | B1 | 2/2003 | Castleman |
| 6,673,248 | B2 | 1/2004 | Chowdhury |
| 6,764,659 | B2 | 7/2004 | Perlov et al. |
| 7,375,348 | B1 | 5/2008 | Sickenberger et al. |
| 8,298,418 | B2 | 10/2012 | Liechti et al. |
| 2001/0042843 | A1 | 11/2001 | Cox et al. |
| 2003/0030011 | A1 | 2/2003 | Brown et al. |
| 2004/0018630 | A1 | 1/2004 | Birks et al. |
| 2004/0052702 | A1 | 3/2004 | Shuman et al. |
| 2004/0097021 | A1 | 5/2004 | Augusto et al. |
| 2004/0241868 | A1 | 12/2004 | Cox et al. |
| 2005/0103723 | A1 | 5/2005 | Wilkins et al. |
| 2005/0160791 | A1 | 7/2005 | Kung |
| 2006/0240558 | A1 | 10/2006 | Zhao |
| 2008/0116054 | A1 | 5/2008 | Leach et al. |
| 2008/0304048 | A1 | 12/2008 | Tormod |
| 2009/0120473 | A1 | 5/2009 | Lynn |
| 2009/0302230 | A1 | 12/2009 | Birks et al. |
| 2010/0027016 | A1 | 2/2010 | Birks et al. |
| 2010/0061885 | A1 | 3/2010 | Harley |
| 2010/0159601 | A1 | 6/2010 | Patton |
| 2010/0212406 | A1 | 8/2010 | Browne et al. |
| 2011/0147580 | A1 | 6/2011 | Bell et al. |
| 2011/0164245 | A1 | 7/2011 | Eikelmann et al. |
| 2011/0201123 | A1 | 8/2011 | Watson et al. |
| 2012/0006098 | A1 | 1/2012 | Degner et al. |
| 2012/0135396 | A1 | 5/2012 | McDevitt et al. |
| 2013/0045496 | A1 | 2/2013 | Jansen |
| 2013/0270429 | A1 | 10/2013 | Bilenko et al. |
| 2013/0292581 | A1 | 11/2013 | Russell et al. |
| 2014/0034840 | A1* | 2/2014 | Davenport ............ G01N 21/33 250/370.01 |
| 2014/0106463 | A1 | 4/2014 | Wald et al. |
| 2015/0070889 | A1 | 3/2015 | Sooferian |
| 2015/0037772 | A1 | 12/2015 | Birks et al. |
| 2015/0362426 | A1 | 12/2015 | Nishino et al. |
| 2016/0103089 | A1 | 4/2016 | Boyette et al. |
| 2016/0187214 | A1 | 6/2016 | Al-Hemyari |
| 2017/0115272 | A1 | 4/2017 | Rihani et al. |
| 2017/0219479 | A1 | 8/2017 | Bilenko et al. |
| 2019/0056317 | A1 | 2/2019 | Clausen et al. |

OTHER PUBLICATIONS

International Search Report and Written Opinion for the International Patent Application No. PCT/US18/015019, dated Apr. 6, 2018, 10 pages.
International Search Report and Written Opinion for the International Patent Application No. PCT/US18/14768, dated Apr. 5, 2018, 8 pages.
International Search Report and Written Opinion for the International Patent Application No. PCT/US18/15846, dated Mar. 29, 2018, 9 pages.
International Search Report and Written Opinion for the International Patent Application No. PCT/US18/17601, dated May 7, 2018, 7 pages.
International Search Report and Written Opinion for the International Patent Application No. PCT/US18/14841, dated Mar. 29, 2018, 7 pages.
Nikoleav et al. "Atmospheric Ozone Concentration Measurement by UV Light-Emitting Diode Radiation Absorption" Bulletin of the Lebedev Physics Institute. 2013, vol. 40 (2), pp. 50-53.

* cited by examiner

SYSTEM AND METHOD FOR OZONE CONCENTRATION MEASUREMENT IN ICE

This is a national stage application filed under 35 U.S.C. § 371 of pending international application PCT/US2018/014841, filed Jan. 23, 2018, the entirety of which application is hereby incorporated by reference herein.

FIELD

The present embodiments relate to gas concentration measurement devices, more particularly, to an apparatus suitable for measuring ozone concentrations in ice.

BACKGROUND

Gas concentration measurement devices are useful to detect the existence or concentrations of various types of gases including ozone. One type of device takes advantage of the optical absorption of light that may pass through a sample of fluid (e.g., air, water) being measured. Ozone is known to strongly absorb light in the short wavelength ultra-violet region of the spectrum, sometimes referred to as UV-C radiation. By placing a source of UV-C radiation at a known distance from a UV-C radiation sensor the concentration of ozone within a fluid sample may be determined by measuring the radiation loss and using known optical formula that calculate the absorption or loss of radiation between source and detector for a given concentration of ozone.

It would be desirable to extend the use of such measurement systems and techniques to measure the presence and concentration of ozone in other states of matter, such as ice. The task of measuring ozone concentration in ice is different from that of measuring ozone concentration in air or in water because ice is not as transparent as water and air. For example, ice pieces can contain bubbles creating during the freezing process. Bubbles are typically located irregularly throughout the ice, and thus calibration procedures used for measuring ozone concentrations in air and water in can't be used.

For example, the process for measuring ozone concentrations in water and air involves comparing UV dissipation in a gap containing air/water having dissolved ozone with UV dissipation in the same gap containing the same air/water but without having dissolved ozone. With ice, however, it is impossible to perform a similar comparison. This is because ice typically contains irregular bubbles, with the result being that there cannot be two equal pieces of ice (with and without ozone) to compare with each other. Rather, each piece of ice will have different absorption and dispersion of UV radiation, independent of ozone concentration.

It would, therefore, be desirable to provide a system and method for measuring ozone concentrations in ice which addresses the aforementioned issues. With respect to these and other considerations, the present disclosure is provided.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

A system is disclosed for determining ozone concentration in ice. The system can include an emitter capable of emitting light containing first and second wavelength bands, the emitter positioned on a first side of a container configured to hold an ice sample. The system can also include first and second detectors, the first detector comprising ultraviolet light sensor (UV sensor) and the second detector comprising a visible light sensor. The first and second detectors may be positioned on a second side of the container, the second side being opposite the first side. A semitransparent mirror or quartz window may be positioned between the container and the first and second detectors, the semitransparent mirror or quartz window for receiving light from the emitter and splitting it into a UV portion and a visible portion. The UV portion may be directed to the first detector and the visible portion directed to the second detector. The first wavelength band can be about 250 nanometers (nm) and the second wavelength band can be greater than about 300 nm. The first detector may comprise a solar blind UV photodiode.

The system can further include first and second collimation screens, the first collimation screen positioned between the emitter and the container, the second collimation screen positioned between the container and the semitransparent mirror or quartz window. The first and second collimation screens can be configured for orienting the elements of the light from the emitter to be parallel. The first and second detectors may be narrow band light detectors. The first and second detectors may be broadband light detectors. The apparatus may further include first and second filters associated with the first and second detectors, respectively, for transmitting radiation having first and second bandwidths to the first and second detectors. The container may be UV-transparent.

The system can further include an amplifier and a microprocessor associated with at least one of the first and second detectors. The amplifier and microprocessor may be configured to amplify a signal from the respective detector and manipulate received information to obtain one or more outputs that are representative of the concentration of ozone in the ice sample A system is disclosed for determining ozone concentration in ice. The system may comprise first and second emitters capable of emitting light containing first and second wavelength bands, respectively. The first and second emitters may be positioned on a first side of a container configured to hold an ice sample. The system may also include first and second detectors, the first detector comprising ultraviolet light sensor (UV sensor) and the second detector comprising a visible light sensor. The first and second detectors may be positioned on a second side of the container, the second side being opposite the first side. A semitransparent mirror or quartz window may be positioned between the container and the first and second detectors. The semitransparent mirror or quartz window may be configured for receiving light from the first and second emitters and splitting it into a UV portion and a visible portion, the UV portion directed to the first detector and the visible portion directed to the second detector. The first wavelength band may be about 250 nanometers (nm) and the second wavelength band may be greater than about 300 nm.

The system may further comprise first and second lenses associated with the first and second emitters, respectively. The first lens may be configured for orienting the elements of the light from the first emitter to be parallel, the second lens may be configured for orienting the elements of the light from the second emitter to be parallel. The system further may comprise a mirror positioned to reflect light from the first and second emitters and to directed a combined light beam through the container. The first emitter can include a UV-LED power supply. The first emitter can be a UV-LED and the second emitter can be a visible-LED. The first detector can be a solar blind UV photodiode. The container can be UV-transparent.

The system may further include an amplifier and a microprocessor associated with at least one of the first and second detectors. The amplifier and microprocessor may be configured to amplify a signal from the respective detector and manipulate received information to obtain one or more outputs that are representative of the concentration of ozone in the ice sample.

Figure 1:
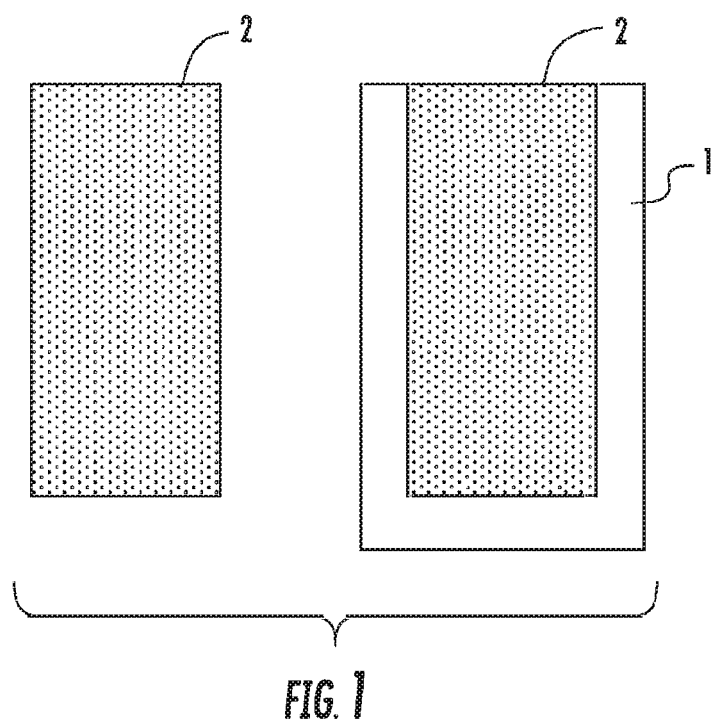
FIG. 1 depicts a cross-section view of an ice sample, and an ice sample disposed within a container, according to various embodiments of the disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. In the drawings, like numbering represents like elements.

Furthermore, certain elements in some of the figures may be omitted, or illustrated not-to-scale, for illustrative clarity. The cross-sectional views may be in the form of "slices", or "near-sighted" cross-sectional views, omitting certain background lines otherwise visible in a "true" cross-sectional view, for illustrative clarity. Furthermore, for clarity, some reference numbers may be omitted in certain drawings.

DETAILED DESCRIPTION

The present embodiments will now be described more fully hereinafter with reference to the accompanying drawings, in which some embodiments are shown. The subject matter of the present disclosure, however, may be embodied in many different forms and should not be construed as limited to the embodiments set forth herein. Rather, these embodiments are provided so that this disclosure will be thorough and complete, and will fully convey the scope of the subject matter to those skilled in the art. In the drawings, like numbers refer to like elements throughout.

Ice is widely used in the food industry to increase the usable life of food products as compared to unfrozen food products. One issue with using ice to freeze or otherwise cool food products using ice, however, is that if the water used to make the ice is contaminated with bacteria, that bacteria can be transferred to the food product when it is thawed. And although the presence of ice may retard growth of bacteria that is present on the frozen or cooled food product, it will not eliminate or kill the bacteria. As will be appreciated, the presence of bacteria on the surface of food products can be a problem for consumers when bacterial contamination of preparation surfaces, or the ultimately consumed food product, occurs.

Ozone can be used to kill bacteria. When ozone molecules come into contact with the cell wall of the bacterium, a reaction called an oxidative burst occurs which creates a hole in the cell wall. This hole in the cell wall injures the bacterium, causing it to lose its shape while ozone molecules continue creating holes in the cell wall. After thousands of ozone collisions over only a few seconds, the bacterial wall can no longer maintain its shape and the cell dies.

It will be appreciated that by freezing water saturated with ozone, the resulting ice product can have the aforementioned antibacterial effect. That is, as ozone is released from the ice (e.g., through melting or sublimation) the released ozone will kill bacteria on or near the food product surface, thus decontaminating the food product. The disclosed apparatus and techniques can be used to control an initial ozone concentration in ice, such as by measuring one or more produced ice samples. The disclosed apparatus and techniques can also be used to characterize the ozone decay process in ice samples as a function of time after water freezing as a function of water content, again by measuring ozone concentration in one or more produced ice samples over time.

In various embodiments improved gas concentration measurement apparatus and techniques are presented. The present embodiments may be usefully employed for detection of gas concentrations for UV-absorbing gases, such as ozone. In particular, example non-limiting embodiments are related to optically transparent apparatus, sometimes referred to as a cuvette, containing ice. As will be appreciated, a cuvette 1 (FIG. 1) may be generally optically transparent and may enclose a volume of ice 2 that is deliberately introduced into, or frozen within, the cuvette. And although the disclosure will proceed in relation to a cuvette 1, it will be appreciated that the term cuvette can interpreted to include any appropriate UV-transparent enclosure. As will be described in greater detail below, by employing an emitter to emit electromagnetic radiation into the cuvette on one side and detecting radiation transmitted out of the cuvette on an opposite side, the concentration of ozone contained within the ice 2 in the cuvette 1 may be measured.

Figure 2:
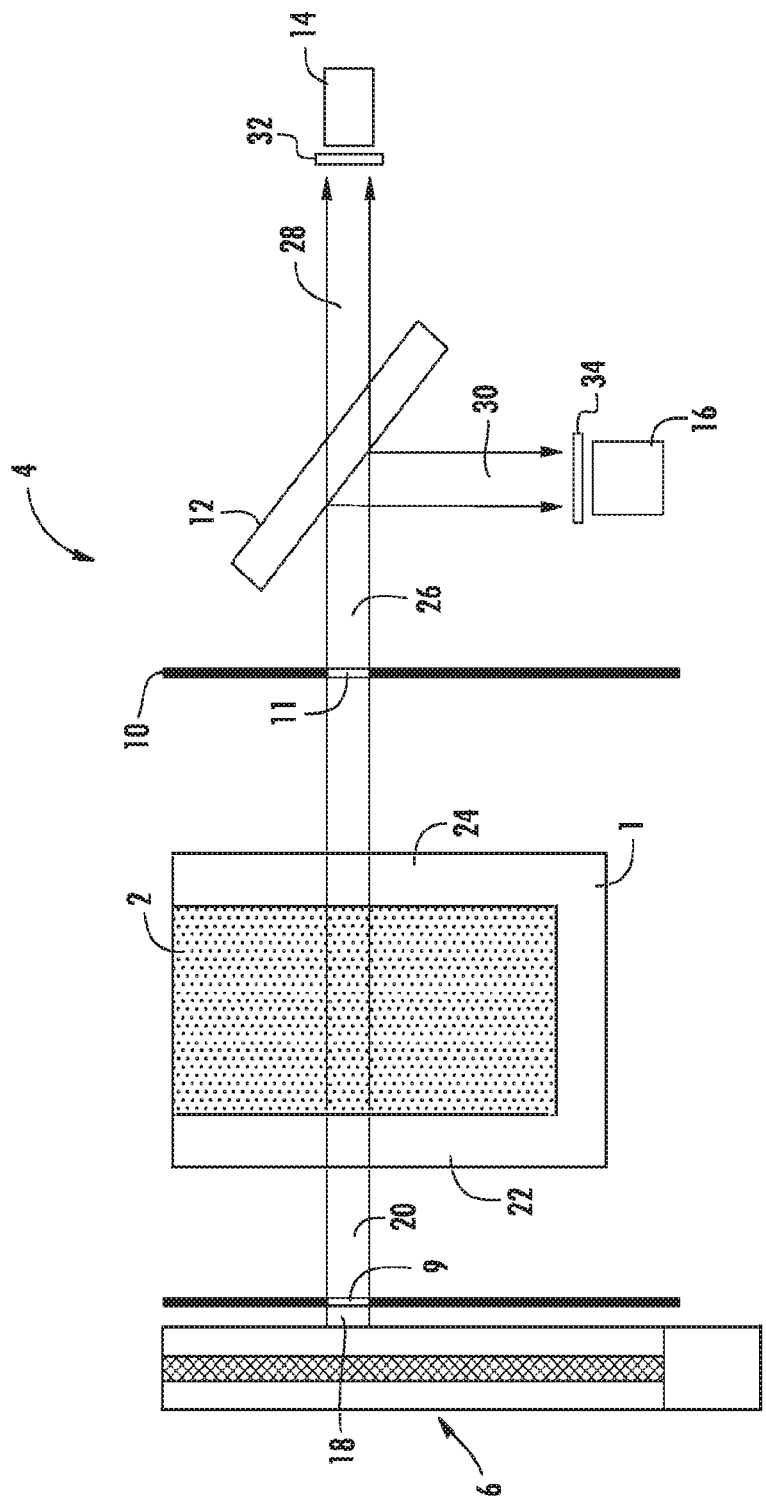
FIG. 2 depicts a side view of an apparatus according to various embodiments of the disclosure.

FIG. 2 illustrates a system 4 for determining a concentration of ozone within an ice sample 2 contained within a cuvette 1. The cuvette 1 may have a rectangular cross-section (in the X-Y plane), square cross-section, circular cross-section, or other convenient shape in various non-limiting embodiments. The system 4 includes an emitter 6, first and second collimation screens 8, 10, a semi-transparent mirror 12, and first and second detectors 14, 16. The emitter 6 may any appropriate light source that includes both visible and ultraviolet (UV) light components. The first detector 14 may be a detector suitable for detecting an intensity of a UV light component emitted by the emitter 6. The second detector 16 may be a detector suitable for detecting an intensity of a visible light component emitted by the emitter 6. Although not shown, the first and second detectors 14, 16 may each include an amplifier and microcontroller for amplifying a signal from the respective detector and manipulating received information to obtain one or more outputs that are representative of the concentration of ozone in the ice sample 2.

To calculate absorption of UV radiation in ice by ozone separate from absorption and dissipation by bubbles, the emitter 6 should be capable of emitting light containing two wavelength bands. The first band should be close the ozone absorption band of UV (e.g., about 250 nanometers (nm)) while second band should be closer to visible light outside the ozone absorption band (e.g., more than 300 nm). The light beam 18 containing the first and second bands can be used to illuminate the ice sample 2. To make a light beam containing the band of UV (about 250 nm) and other band closer to visible light out of ozone absorption band (more than 300 nm). The emitter 6 may be a lamp with a spectrum containing UV and visible light bands. A non-limiting example emitter 6 is a mercury (Hg) quartz lamp, which can be formed into a parallel beam using geometrical collimation by two opaque collimating screens 8, 10 with openings 9, 11, as shown in FIG. 2.

Thus, the light beam 18 may first be collimated by passing the light beam through the first collimation screen 8. As will be appreciated, the first collimation screen 8 will function to ensure that all the elements of the light beam 18 are in line and parallel. The collimated light beam 20 may then be directed through a first side 22 of the cuvette 1, through the ice sample 2, through the second side 24 of the cuvette 1, and through the second collimation screen 10. The resulting collimated light beam 26 may then interact with the semi-transparent mirror 12, which splits the collimated light beam into first and second separate beams 28, 30. As will be appreciated, the first beam 28 may constitute light in the UV band, while the second beam may constitute light in the visible band. It will be appreciated that, in lieu of a semi-transparent mirror 12 a simple quartz window could be used, installed at an angle of about 45° with respect to the incoming collimated light beam 26. A first portion 28 of the collimated light beam will pass through the mirror 12 and will be detected by the first detector 14. The second portion 30 of the collimated light beam is reflected by about 90° such that it is detected by the second detector 16. The first and second light detectors 14, 16 can be appropriate narrow band detectors, or they can be broadband light detectors having appropriate light filters 32, 34 for transmitting radiation with a desired bandwidth to the associated first or second light detector.

Figure 3:
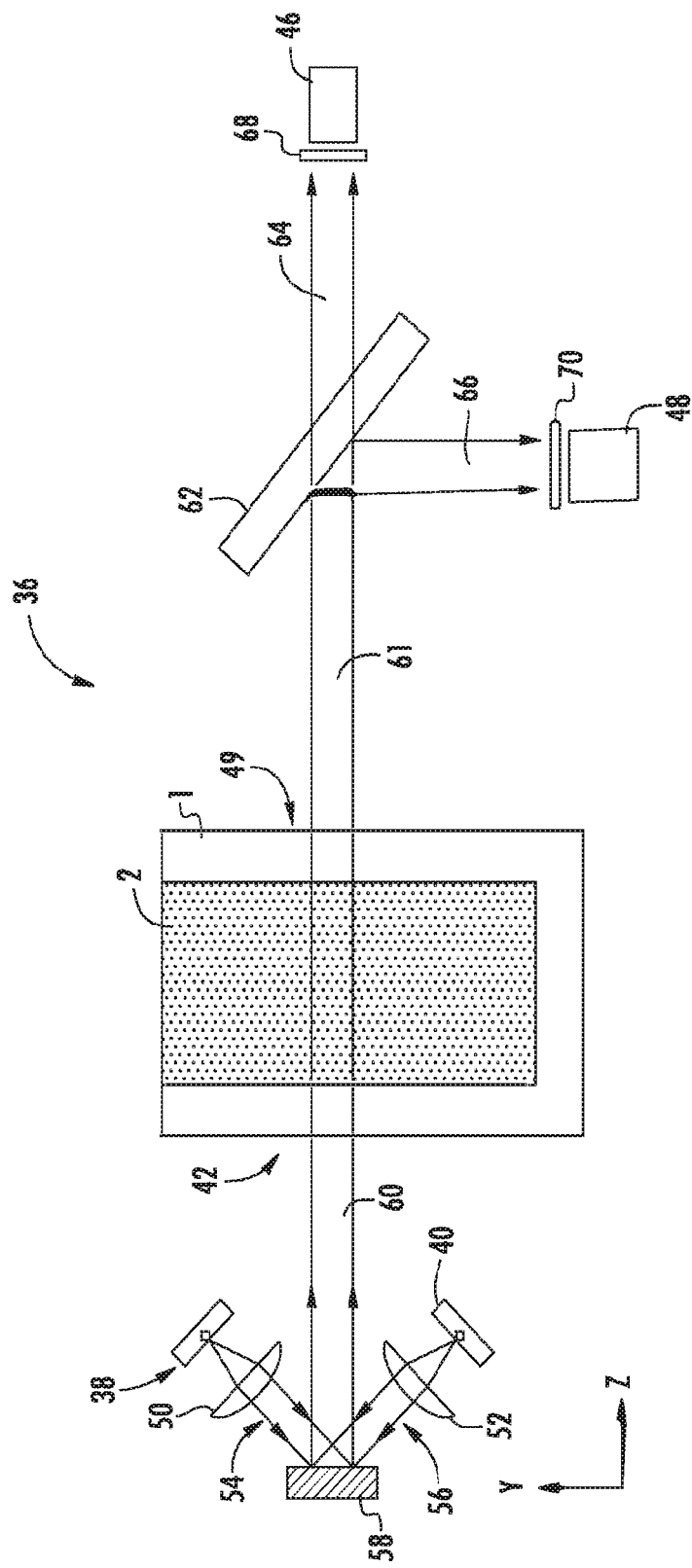
FIG. 3 depicts a side view of another apparatus according to various embodiments of the disclosure.

Referring to FIG. 3, an alternative embodiment of a system 36 for determining a concentration of ozone within an ice sample 2 contained within a cuvette 1 is shown. As will be described, the system 36 of this embodiment includes two LEDs, one of which emits a light beam in the visible spectrum and another of which emits a light beam in the UV spectrum. The two light beams are mixed, and directed through the ice sample 2 in a similar fashion to that described in relation to FIG. 3.

As mentioned, the system 36 may include a bounded volume, such as a cuvette 1, to house an ice sample. The cuvette 1 may have a rectangular cross-section (in the X-Y plane), square cross-section, circular cross-section, or other convenient shape in various non-limiting embodiments. The system 36 may include first and second emitters 38, 40 disposed on a first side 42 of the cuvette 1 and first and second detectors 46, 48 disposed on a second side 49 of the cuvette. The first emitter 38 may include an ultraviolet (UV) light emitting diode (UV-LED), where the UV-LED is designed to emit radiation having a wavelength arranged according to light absorption characteristics of a target gas or gases to be measured in the ice sample 2. In other words, the wavelength or range of wavelengths of radiation emitted by the emitter 104 may be designed to overlap a wavelength or wavelength range where the target gas has a high degree of absorption. In this manner, the presence of a target gas may be detected by the attenuation of electromagnetic radiation directed into the ice sample 2 when at least some photons of the radiation are absorbed by the gas. The second emitter 38 may include a visible light emitting diode (vis-ible-LED) where the visible-LED is designed to emit radiation having a wavelength in the visible range.

In embodiments where the system 36 is used as an ozone detector, the first emitter 38 may include a UV-LED that emits radiation overlapping in wavelength with an optical absorption peak in ozone centered around 260 nanometers (nm) and having a half-width of approximately 20 nm (see also FIG. 4, discussed below). In particular embodiments, the first emitter 38 may include a UV-LED that generates radiation in the range of 250 nm to 300 nm, and more particularly in the range of 250 nm to 270 nm. For example, a known UV LED may be designed to emit radiation over a narrow range, where greater than 75% of the electromagnetic radiation intensity is between 250 nm and 270 nm. This situation ensures that most photons emitted by the first emitter 38 will have a wavelength overlapping a wavelength range of the absorption peak for ozone at 260 nm.

The first and second emitters 38, 40 may include respective first and second emitter lenses 50, 52. The first and second emitter lenses 50, 52 may each have a convex shape, and in some embodiments, may be a hemisphere. By situating the UV-LED 38 at a focus of the first emitter lens 50, light emitted by the UV-LED 38 may have its rays collimated into a first parallel beam of light, shown as beam 54. Likewise, by situating the visible-LED 40 at a focus of the second emitter lens 52, light emitted by the visible-LED 38 may have its rays collimated into a second parallel beam of light, shown as beam 56. The first and second emitter lenses 50, 52 may further be situated and oriented so as to direct the first and second parallel beams 54, 56 toward a mirror 58 which itself is oriented so that the first and second parallel beams are superimposed to form a combined light beam 60 that is directed so that the trajectories of the light rays of the first and second parallel beams (the combined light beam) lie parallel to the long axis (Z-axis) of the system 36.

Turning now to the first and second detectors 46, 48, in various embodiments the first detector 108 may include a UV sensor, such as a solar blind UV photodiode. The term "solar blind" may refer to a detector that is not sensitive to solar radiation at the earth's surface, and in particular, may not be sensitive to radiation having wavelengths greater than 290 nm. As is known, the shortest wavelength of UV solar radiation generally incident at the earth's surface is UV-B radiation, whose range is between about 320 nm and 290 nm. Accordingly, the first detector 46 may not be sensitive to background electromagnetic radiation (also referred to herein as "light") from the sun during normal operation. This insensitivity to background light facilitates more accurate detection of the concentration of a gas such as ozone, since the radiation being measured at first detector 48 may be assumed to be generated from the first emitter 38. The second detector 48 may be a sensor suitable for detecting an intensity of visible light component emitted by the second emitter 40.

Although not shown, the first and second detectors 46, 48 may each include an amplifier and microcontroller for amplifying signals from the respective detector and manipulating received information to obtain one or more outputs that are representative of the concentration of ozone in the ice sample 2.

As with the prior embodiment, the combined light beam 60 may then be directed through a first side 42 of the cuvette 1, through the ice sample 2, and through the second side 49 of the cuvette 1. The resulting combined light beam 61 may then interact with the semitransparent mirror 62, which splits the resulting combined light beam into first and second separate beams 64, 66. The first beam 64 may constitute light in the UV band, while the second beam 66 may constitute light in the visible band. It will be appreciated that, in lieu of a semitransparent mirror 62 a simple quartz window could be used, installed at an angle of about 45° with respect to the resulting combined light beam 61. The first beam 64 will pass through the mirror 62 and will be detected by the first detector 46. The second beam 66 is reflected by about 90° with respect to the resulting combined light beam 61 such that it is detected by the second detector 48. The first and second light detectors 46, 48 can be appropriate narrow band detectors, or they can be broadband light detectors having appropriate light filters 68, 70 for transmitting radiation with a desired bandwidth to the associated first or second light detector.

The first emitter 38 may include a UV-LED power supply (not shown), arranged according to known power supplies to power the first emitter, as well as an amplifier/microcontroller (not shown), coupled to the first detector 46. Likewise, the second emitter 40 may include a visible-LED power supply (not shown), arranged according to known power supplies to power the second emitter, as well as an amplifier/microcontroller (not shown), coupled to the second detector 48.

The cuvette 1 may include a first and second sides 42, 49 that are transparent to UV radiation, in particular, at wavelengths above 250 nm. A suitable UV-transmitting material for use as the cuvette 1, for example, is quartz, where transmission for a 10 millimeter (mm) thick material may exceed 90% at 250 nm wavelength of light. The embodiments are not limited in this context. It will be appreciated that the entirety of the first and second sides 42, 49 need not be transparent, but rather may include respective windows that have the aforementioned transparency, and through which the combined light beam 60 and resulting combined light beam 61 may be directed.

Thus arranged, the first and second emitters 38, 40 may be energized, generating radiation that impinges the mirror 58 and is combined and reflected through the cuvette 1 and ice sample 2 contained therein. As the combined beam 60 traverses the ice sample 2, some photons of the combined beam may be absorbed by a target gas (e.g., ozone) to be measured, due to the optical absorption characteristics of the target gas. By the time the resulting combined beam 61 is split (via mirror 62) and components of which (i.e., first and second beams 64, 66) reach the first and second detectors 46, 48, the intensity of the first and second beams 64, 66 may be reduced from a first intensity at the point of entering the cuvette 1, to a second intensity at the point of exiting the cuvette, where the second intensity is less than the first intensity. The sensed intensities can then be used to determine the concentration of ozone in the ice sample 2.

The process for calculating concentration of ozone in ice will now be described.

The system 4, 36 can initially be zeroed. In the zeroing operation, the cuvette 1 should be removed from the system 4, 36. For the zeroing operation, when the cuvette 1 without an ice sample 2 is disposed in device, a controller of an analog to digital device (e.g., the amplifiers/microcontrollers previously described in relation to FIGS. 2 and 3) takes a digital readings (UOuv) of a signal intensity from respective amplifiers that amplify a signal from the first detector 14, 46, which may be a UV detector. The second detector 16, 48, which may be a visible light detector, likewise takes digital readings (UOvl). On the basis of the detected values of UOuv and UOvl, the parameters Nuv and Nvl may be calculated according to:

$$Nuv = \text{Ln}(U\text{max}/UOuv) \quad \text{Eq. (2.1)},$$

$$Nvl = \text{Ln}(U\text{max}/UOvl) \quad \text{Eq. (2.2)},$$

where Umax is maximal signal for both Analog-to-Digital converters (ADC's), UOuv is the digital reading of a Digital-to-Analog converter (DAC) at the moment of zeroing for the UV channel and UOvl is the digital reading of a DAC at the moment of zeroing for the visible light channel, and Ln is a natural logarithm. In one non-limiting example embodiment, Umax may read 4.5 V, while UOuv and UOvl may read 3 V, without an ice sample present.

The cuvette 1 with an ice sample 2 may then be inserted in device 4, 36. Intensity readings may then be collected by the system 4, 36 and can be used to calculate ozone concentration (C) in the ice sample. In some embodiments, the calculated ozone concentration (C) can be indicated on a user display screen or may be sent by UART port or other appropriate port to other devices as appropriate.

In some embodiments, C may be calculated according to the following equation:

$$C = ((\text{Ln}(U\text{max}/Uuv.av) - Nuv) - (\text{Ln}(U\text{max}/Uvl.av) - Nvl)) * K \quad \text{Eq. (3)},$$

where Uuv.av and Uvl.av are the averages, respectively, of actual digital readings of a DAC's of the UV channel and the visible light channel respectively obtained during a given time.

As a non-limiting example, a sampling interval for taking the digital readings in the presence of ozone may be from 1 second to 20 seconds. It will be appreciated, however, that the embodiments are not limited in this context. The number of digital readings may vary, while in one implementation a reading may be taken every 0.1 seconds, meaning a sample size for calculating Uav may range up to 100 readings or more. Again, it will be appreciated that the embodiments are not limited in this context.

Following the above example where U0 is 3 V, the value of Uav may be 2.0 V, indicating the absorption of some of the radiation by the ozone. In some implementations, time of averaging may be installed in a program menu. K can represent a calibrating coefficient (which may be implemented in a program menu). Where ozone is present in the ice sample 2, raw readings from the first detector 14, 46 can be adjusted by K to achieve an actual ozone concentration. The value of K can be determined based on testing or other appropriate technique. According to various embodiments, ozone concentrations of approximately 0.1 g/m$^3$ to 30 g/m$^3$ may readily be measured.

Figure 4:
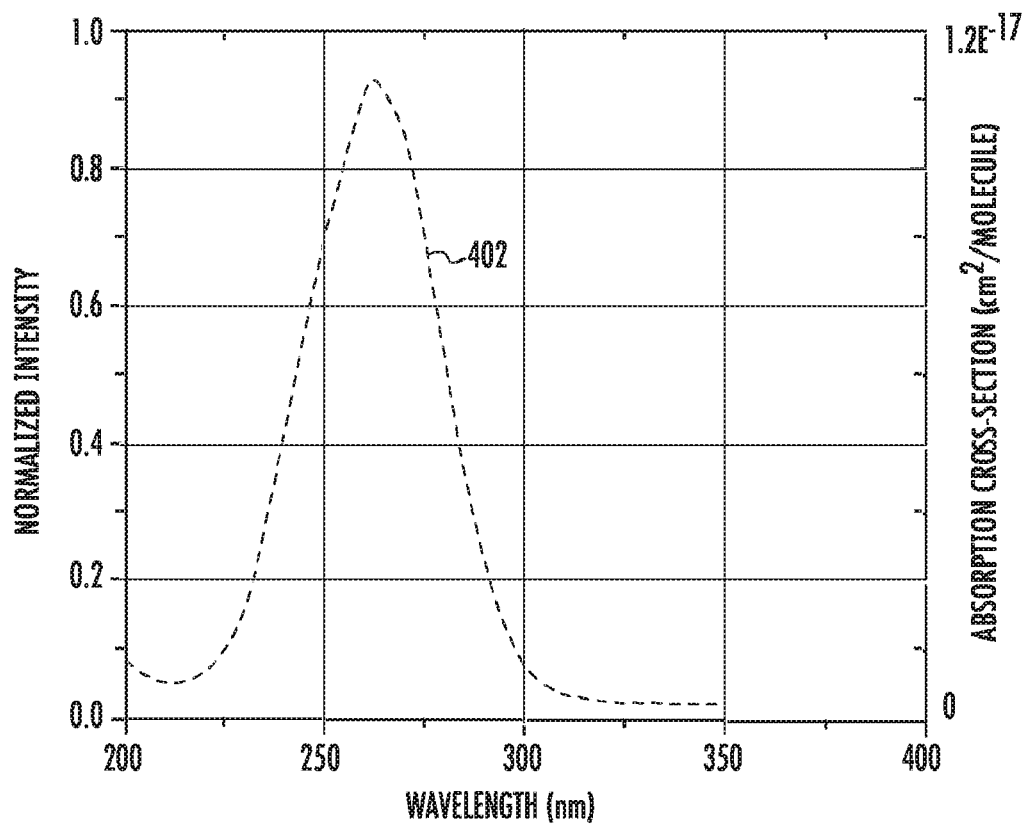
FIG. 4 is a composite graph depicting optical properties of ozone and an emitter, according to an embodiment of the disclosure.

To further illustrate the operating principles of an apparatus according to the present embodiments, FIG. 4 is a composite graph depicting optical properties of ozone and an emitter, according to an embodiment of the disclosure. In FIG. 4 a curve 402 illustrates an absorption peak for ozone, showing that the cross-section for absorption has a maximum at approximately 260 nm, while no absorption of light takes place above approximately 325 nm.

Figure 5:
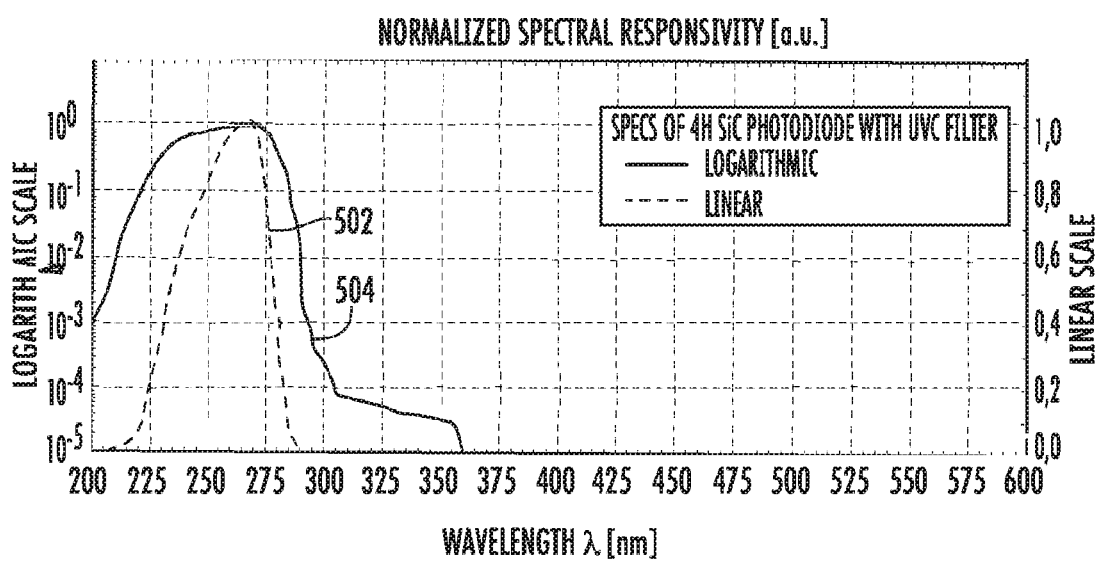
FIG. 5 is graph depicting optical properties of a detector according to an embodiment of the disclosure.

To further illustrate principles of detection, FIG. 5 is graph depicting optical properties of a detector according to an embodiment of the disclosure. In FIG. 5, the same data of silicon carbide photodiode with a radiation filter is shown as two different curves, linear curve 502, and logarithmic curve 504. As shown, a peak in responsivity takes place at 270 nm, while little radiation is detected above 290 nm wavelength. Accordingly, the detector device providing the data of FIG. 5 is suitable to detect radiation generated by the disclosed emitter device.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are in the tended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Thus, the claims set forth below should be construed in view of the full breadth and spirit of the present disclosure as described herein.

What is claimed is:

1. A system for determining ozone concentration in ice, comprising:
   an emitter configured to emit light containing first and second wavelength bands, wherein one of the first and second wavelength bands comprises a UV light component and the other one of the first and second bands comprises a visible light component respectively, the emitter positioned on a first side of a container configured to hold an ice sample; and
   first and second detectors, the first detector comprising ultraviolet light sensor (UV sensor) and the second detector comprising a visible light sensor, the first and second detectors positioned on a second side of the container, the second side being opposite the first side;
   a semitransparent mirror or quartz window positioned in between a side surface of the container and the first and second detectors, the semitransparent mirror or quartz window configured to receive light from the emitter and configured to split the light into a UV portion and a visible portion, the UV portion directed to the first detector and the visible portion directed to the second detector.

2. The system of claim 1, wherein the first wavelength band is about 250 nanometers (nm) and the second wavelength band is greater than about 300 nm.

3. The system of claim 1, wherein the first detector comprises a solar blind UV photodiode.

4. The system of claim 1, further comprising first and second collimation screens, the first collimation screen positioned between the emitter and the container, the second collimation screen positioned between the container and the semitransparent mirror or quartz window.

5. The system of claim 4, the first and second collimation screens for orienting the elements of the light from the emitter to be parallel.

6. The system of claim 1, wherein the first and second detectors are narrow band light detectors.

7. The system of claim 1, wherein the first and second detectors are broadband light detectors, the apparatus further including first and second filters associated with the first and second detectors, respectively, for transmitting radiation having first and second bandwidths to the first and second detectors.

8. The system of claim 1, wherein the container is UV-transparent.

9. The system of claim 1, further comprising an amplifier and a microprocessor associated with at least one of the first and second detectors.

10. The system of claim 1, the amplifier and microprocessor for amplifying a signal from the respective detector and manipulating received information to obtain one or more outputs that are representative of the concentration of ozone in the ice sample.

11. A system for determining ozone concentration in ice, comprising:
   first and second emitters an emitter configured to emit light first and second wavelength bands, wherein one of the first and second wavelength bands comprises a UV light component and the other one of the first and second bands comprises a visible light component, respectively, the first and second emitters positioned on a first side of a container configured to hold an ice sample; and
   first and second detectors, the first detector comprising ultraviolet light sensor (UV sensor) and the second detector comprising a visible light sensor, the first and second detectors positioned on a second side of the container, the second side being opposite the first side;
   a semitransparent mirror or quartz window positioned in between a side surface of the container and the first and second detectors, the semitransparent mirror or quartz window configured to receive light from the first and second emitters and configured to split the light into a UV portion and a visible portion, the UV portion directed to the first detector and the visible portion directed to the second detector.

12. The system of claim 11, wherein the first wavelength band is about 250 nanometers (nm) and the second wavelength band is greater than about 300 nm.

13. The system of claim 11, further comprising first and second lenses associated with the first and second emitters, respectively, the first lens for orienting the elements of the light from the first emitter to be parallel, the second lens for orienting the elements of the light from the second emitter to be parallel.

14. The system of claim 11, further comprising a mirror positioned to reflect light from the first and second emitters and to directed a combined light beam through the container.

15. The system of claim 11, wherein the first emitter includes a UV-LED power supply.

16. The system of claim 11, wherein the first emitter is a UV-LED and the second emitter is a visible-LED.

17. The apparatus of claim 16, wherein the first detector is a solar blind UV photodiode.

18. The system of claim 11, wherein the container is UV-transparent.

19. The system of claim 11, further comprising an amplifier and a microprocessor associated with at least one of the first and second detectors.

20. The system of claim 11, the amplifier and microprocessor for amplifying a signal from the respective detector and manipulating received information to obtain one or more outputs that are representative of the concentration of ozone in the ice sample.

* * * * *